(12) United States Patent
Griffin et al.

(10) Patent No.: US 7,575,871 B2
(45) Date of Patent: Aug. 18, 2009

(54) METHOD OF DIAGNOSIS AND KIT OF PARTS THEREFOR

(75) Inventors: Martin Griffin, Nottingham (GB); Brian Gibbons, Nottingham (GB)

(73) Assignee: Aston University, Birmingham (GB)

( * ) Notice: Subject to any disclaimer, the term of this patent is extended or adjusted under 35 U.S.C. 154(b) by 255 days.

(21) Appl. No.: 10/484,404

(22) PCT Filed: Jul. 18, 2002

(86) PCT No.: PCT/GB02/03276

§ 371 (c)(1),
(2), (4) Date: Jun. 28, 2004

(87) PCT Pub. No.: WO03/008976

PCT Pub. Date: Jan. 30, 2003

(65) Prior Publication Data

US 2004/0248193 A1 Dec. 9, 2004

(30) Foreign Application Priority Data

Jul. 21, 2001 (GB) .................................. 0117870.6

(51) Int. Cl.
*G01N 33/53* (2006.01)
*G01N 33/00* (2006.01)
(52) U.S. Cl. ...................... 435/7.1; 435/7.92
(58) Field of Classification Search ........................ None
See application file for complete search history.

(56) References Cited

U.S. PATENT DOCUMENTS 5,654,168 A 8/1997 Bujard et al.
6,319,726 B1 * 11/2001 Schuppan et al. ........... 436/506

FOREIGN PATENT DOCUMENTS

WO   WO 98/03872   1/1998
WO   WO 98/15836   4/1998
WO   WO 02/086509  10/2002

OTHER PUBLICATIONS

Marttinen et al., 1993, Pediatric Research, vol. 34: 420-423.*
Aeschlimann et al., 2000, Conn. Tissue Res. vol. 41: 1-27.*
Korponay-Szabo et al., 2003, Gut, vol. 52: 199-204.*
Valeski et al., 1990, Int. Arch. Allergy, vol. 93: 1-7.*
Chao et al., 1996, Cytometry, vol. 23: 48-53.*
Dorland's Illustrated Medical Dicitonary, 2004, pp. 1-2.*
Begos et al., "Metachronous Small-Bowel Adenocarcinoma in Celiac Sprue", *J Clin. Gastroenterol*, 20(3):233-236 (1995).
Clemente et al., "Immune Reaction Against the Cytoskeleton in Coeliac Disease", XP009011811.
Dieterich et al., "Identification of Tissue Transglutaminase as the Autoantigen of Celiac Disease", *Nature Medicine*, 3(7):797-801 (1997).
Dieterich et al., "Characterization of the Autoantigens in Coeliac Disease". XP-002243230.
Gentile et al., "Isolation and Characterization of cDNA Clones to Mouse Macrophage and Human Endothelial Cell Tissue Transglutaminases", *The Journal of Biological Chemistry*, 266(1):478-483 (1991).
Greenberg et al., "Transglutaminases: Multifunctional Cross-Linking Enzymes That Stabilize Tissues", *The FASEB Journal*, 5:3071-3077 (1991).
Logan et al., "Mortality in Celiac Disease", *Gastroenterology*, 97:265-271 (1989).
Mäki, "The Humoral Immune System in Coeliac Disease", *Bailliére's Clinical Gastroenterology*, 9(2): 231-249 (1995).
Sblatterto et al., "Human Recombinate Tissue Transglutaminase ELISA: An Innovative Diagnostic Assay for Celiac Disease", *The American Journal of Gastroenterology*, 95(5):1253-1257 (2000).
Sollid, "Molecular Basis of Celiac Disease", *Annu. Rev. Immunol.*, 18:53-81 (2000).
Verderio et al., "Regulated Expression of Tissue Transglutaminase in Swiss 3T3 Fibroblasts: Effects on the Processing of Fibronectin, Cell Attachment, and Cell Death", *Experimental Cell Research*, 239:119-138 (1998).
Barsigian, C. et al. (Nov. 25, 1991). "Tissue (Type II) Transglutaminase Covalently Incorporates Itself, Fibrinogen, or Fibronectin into High Molecular Weight Complexes on the Extracellular Surface of Isolated Hepatocytes," *J. Biol. Chem.* 266(33):22501-22509.
Gaudry, C.A. et al. (Oct. 22, 1999). "Cell Surface Localization of Tissue Transglutaminase Is Dependent on a Fibronectin-binding Site in Its N-terminal β-Sandwich Domain," *J. Biol. Chem.* 274(43):30707-30714.
Ghedira, I. et al. (2001). "Anticorps Anti-Endomysium, Anti-Réticuline at Anti-Giladine, Intérêt Dans le Diagnostic de la Maladie Coeliaque Chez L'Enfant," *Pathol. Biol.* 49:47-52. (English-language machine translation, six pages.).
Kojima, S. et al. (Apr. 1, 1993). "Requirement for Transglutaminase in the Activation of Latent Transforming Growth Factor-β in Bovine Endothelial Cells," *J. Cell Biol.* 121(2):439-448.
Nunes, I. et al.(Mar. 10. 1997). "Latent Transforming Growth Factor-β Binding Protein Domains Involved in Activation and Transglutaminase-dependent Cross-Linking of Latent Transforming Growth Factor-β," *J. Cell Biol.* 136(5):1151-1163.

* cited by examiner

*Primary Examiner*—Michael Szperka
*Assistant Examiner*—Amy E Juedes
(74) *Attorney, Agent, or Firm*—Morrison & Foerster LLP (57) ABSTRACT

A method for diagnosing coeliac disease in a patient comprising (a) providing an antibody sample from the patient to be tested, (b) contacting said antibody sample with cross-linked extracellular matrix (ECM) material immobilized on a surface and (c) detecting binding of antibodies present in the sample to the ECM-coated surface, wherein the binding of antibodies present in the sample to the ECM-coated surface being indicative of a positive diagnosis. Preferably, step (c) comprises an ELISA. The invention further provides a kit of parts for use in diagnosing coeliac disease in a patient.

15 Claims, 3 Drawing Sheets

METHOD OF DIAGNOSIS AND KIT OF PARTS THEREFOR

CROSS-REFERENCE TO RELATED APPLICATIONS

This application is a National Phase application under 35 U.S.C. § 371 of International Application No. PCT/GB2002/03276 filed Jul. 18, 2002 and claims the benefit of Great Britain Application No. 0117870.6 filed Jul. 21, 2001.

The present invention relates to a method of diagnosing coeliac disease. The invention further provides a kit of parts for the diagnosis of coeliac disease.

BACKGROUND

Coeliac disease (CD) is a complex immunological response to the presence of wheat gluten in the gut. Generally the disease manifests through malabsorption of the upper small intestine caused by villus atrophy and crypt hyperplasia resulting from the inappropriate immune response to gluten in this region. Symptoms of the disease often reflect the malabsorption occurring in the gut, i.e. growth defects, anaemia and diarrhoea although asymptomatic patients are common. If left untreated the disease may lead to complications such as small intestinal lymphoma (Logan et al., 1989, *Gastroenterology* 97:265-271), and small bowel adenocarcinoma (Begos et al., 1995, *J Clin Gastroenterol* 20:233-6).

Until recently the recognised method of diagnosis for coeliac disease as defined by the European Society for Paediatric Gastroenterology and Nutrition (ESPGAN) was a source of considerable stress to patients due to repeated intestinal biopsy over long periods of time. Extensive research into the progression of the disease and into non-invasive tools for its diagnosis has led to the identification of several broadly defined serological markers. In the light of these discoveries EPSGAN have revised their criteria for CD diagnosis (Walker-Smith et al, 1990, *Report of working group of European Society of Pediatric Gastroenterology and Nutrition*) so that biopsy is limited to one sample, taken at presentation, along with the presence of recognised CD serological markers that diminish with gluten withdrawal from the diet. Thus the research emphasis has shifted in recent years to the search for a serological test that is as at least as good as gut biopsy for CD diagnosis.

To date, the humoral aspect of coeliac disease has been grouped according to the antigens with which reaction has been shown in in vitro assays. Thus both IgG and IgA class anti-gliadin antibodies (AGA), anti-reticulin antibodies (ARA), and anti-endomysial antibodies (EMA) have been defined and investigated. Many papers, reviews and trials have been published on the relative efficacy of using each of these markers in various assay formats and each approach has its champion. Doubts over the specificity of AGA have persisted as it has become apparent that limited immune responses to gliadin along with other recognised food antigens can occur in a variety of gut disorders (Maki et al, 1995, In Howdle P D (ed): Coeliac Disease, *Baillières Clin Gastroenterol* 9:231-249). Of the other two groups of antibody the EMA have risen to prominence with the discovery by Dieterich et al. (1997, *Nature Med* 3:797-801) that Type II transglutaminase could be precipitated from cell extracts using AGA depleted serum from patients with chronic CD. The human Type II TG based ELISAs that rapidly followed proved to be both highly specific and sensitive and were obviously widely welcomed as a replacement for the antiquated and difficult to interpret immunofluorescent test using monkey oesophagus or human placenta sections.

It was soon apparent however that the results of clinical use of type II TG based assays very often failed to match these high levels of reliability. This inconsistency in the results may reflect the fact that much of the original research has been performed using sera from chronic coeliac patients whereas the clinical use of the assay has seen a wider variety of patients that have presented the disease in differing degrees of severity.

In addition to the poor clinical results seen with type II TG based ELISAs it is now becoming clear that several other antigens are involved in the autoimmune aspect of coeliac disease (Clemente et al., 2000, *Gut* 47:520-526) and that the original inference of Dieterich that type II TG is the only significant antigen has become invalid.

Hence, there is a need to improved methods of diagnosing coeliac disease.

SUMMARY OF THE INVENTION

Accordingly, a first aspect of the invention provides method for diagnosing coeliac disease in a patient comprising:

(a) providing an antibody sample from the patient to be tested;

(b) contacting said antibody sample with cross-linked extracellular matrix (ECM) material immobilised on a surface; and (c) detecting binding of antibodies present in the sample to the ECM-coated surface wherein the binding of antibodies present in the sample to the ECM-coated surface is indicated of a positive diagnosis.

Preferably, the antibody sample is a serum sample. Alternatively, the antibody sample may be a saliva sample.

Conveniently, the antibody sample comprises IgA antibodies.

By 'cross-linked extracellular matrix (ECM) material' we mean proteins secreted by cells which are deposited in an insoluble matrix surrounding the cells or are specific to a particular cell membrane. Proteins normally associated with the ECM include fibronectin, vitronectin, collagens, latent TGFβ-1 binding protein (LTBP-1), fibrillins, elastin and laminin. (Comper, W D, 1996, *Extracellular matrix*, Vol I and II, Harwood Acad. Pubs, Amsterdam, Netherlands).

Preferably, the ECM is cross-linked by the action of a tissue transglutaminase enzyme, which catalyzes the formation of inter- and intra-protein ε(γ-glutamyl) isopeptide bonds and the incorporation of polyamines at certain glutamine residues (Greenberg, C. S., Birckbichler, P. J. and Rice, R. H. (1991) *FASEB J.* 5, 3071-3077).

Conveniently, the ECM material is adhered to the surface.

Preferably, ECM is derived from cells which express a tissue transglutaminase. Advantageously, the ECM is derived from mammalian cells, for example human or murine cells.

Thus, the method comprises measuring antibodies in a sample from the patient to be tested which have affinity for antigenic components of the cross-linked ECM material. For example, the antibodies may have affinity for extracellular matrix proteins, tissue transglutaminase or novel products of the cross-linking activity of the transglutaminase on the extracellular matrix proteins.

Advantageously, step (c) comprises simultaneously detecting binding of two or more types of antibody, each type of antibody having affinity for a different component of the cross-linked ECM.

Preferably, step (c) comprises detecting binding of IgA antibodies to the ECM-coated surface.

Alternatively, step (c) comprises detecting binding of IgG antibodies to the ECM-coated surface.

In a preferred embodiment of the first aspect of the invention, a diagnosis is obtained by comparing the level of binding of antibodies in the sample from the patient to the level of binding of antibodies in an antibody sample from a donor who does not have coeliac disease. Thus, the method may further comprise repeating steps (b) and (c) with a negative control sample. Conveniently, the negative control sample is a serum sample or a saliva sample from a normal healthy individual.

Preferably, a positive diagnosis is made when the level of binding of antibodies present in the patient's sample to the ECM-coated surface is at least 20%, 30%, 40%, 50%, 100%, 200% or more greater than the level of binding of antibodies present in the negative control sample. More preferably, a positive diagnosis is made when the level of binding of antibodies present in the patient's sample to the ECM-coated surface is at least 100% greater than the level of binding of antibodies present in the negative control sample.

In a preferred embodiment of the first aspect of the invention, step (c) comprises using an enzyme-linked immunosorbent assay (ELISA). Such methodology is well-known in the art (for example, see Sblattero et al, 2000, *Am J. Gastroenterol.* 95:1253-57).

In conventional (indirect) ELISAs, the binding of a (primary) antibody to a target antigen is detected by means of a secondary antibody with affinity for the primary antibody. The secondary antibody is conjugated to an enzyme, such as horse radish peroxidase, which catalyses the transformation of a non-detectable substrate to a detectable product. Thus, the detectable product gives a measure of the binding of the primary antibody. Often, the detectable product is coloured and may be detected by spectrophotometry.

In the methods of the invention, the target molecules are anti-ECM antibodies present in the antibody sample from the patient to be tested, hence direct ELISAs may be used in which an anti-human Ig antibody conjugated to a enzyme such as horse-radish peroxidase (HRP) is applied directly to the sample to be tested.

Advantageously, the ELISA comprises using an anti-human IgA antibody conjugated to HRP to detect binding of antibodies in sera or saliva samples to the cross-linked ECM.

A second aspect of the invention provides a kit of parts for diagnosing coeliac disease for use in the method of the invention, the kit comprising (a) a surface upon which cross-linked extracellular matrix (ECM) material is immobilised or means for producing such as surface; and (b) means for detecting binding to said ECM material of antibodies produced by persons suffering from coeliac disease.

Preferably, the kit comprises a surface upon which cross-linked ECM material is immobilised. Advantageously, the ECM material is adhered to the surface. Conveniently, the cross-linked ECM material is derived from cells which secrete and deposit ECM and which express a tissue transglutaminase. For example, the cells may be human foreskin dermal fibroblasts. Suitably, the cells naturally express a tissue transglutaminase at high levels.

In an alternative embodiment, the cross-linked ECM material is derived from cells capable of secreting and depositing ECM which naturally express low levels of a tissue transglutaminase (or which do not naturally express a tissue transglutaminase) but are transfected with a nucleic acid molecule encoding a transglutaminase so that expression of the enzyme is increased. Preferably, the cells are fibroblast cells, such as Swiss 3T3 fibroblast cells, transfected with a nucleic acid molecule encoding tissue transglutaminase, as described in Verderio et al. (1998) *Exp. Cell Res.* 239:119-38.

By 'a transglutaminase' we mean a member of the group of enzymes identified by Enzyme Commission System of Classification No. 2.3.2.13 (EC 2.3.2.13). Preferably, the transglutaminase is human type II transglutaminase.

Exemplary nucleotide sequences encoding tissue transglutaminase are known in the art. For example, the coding sequence for human tissue transglutaminase is disclosed in Gentile et al, 1991, *J. Biol. Chem.* 266(1) 478-483 (Accession no. M55153).

Nucleic acid molecules encoding a transglutaminase may be used in accordance with known techniques, appropriately modified in view of the teachings contained herein, to construct an expression vector, which is then used to transform an appropriate host cell for the expression and production of the polypeptide of the invention. Methods of expressing proteins in recombinant cells lines are widely known in the art (for example, see Sambrook & Russell, 2001, *Molecular Cloning, A Laboratory Manual*, Third Edition, Cold Spring Harbor, N.Y.). Exemplary techniques also include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,852,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker.

In brief, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation (e.g. see WO 98/16643).

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. Such markers include dihydrofolate reductase, G418 or neomycin resistance for eukaryotic cell culture. Alternatively, the gene for such a selectable trait can be on another vector, which is used to co-transform the desired host cell.

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. Examples of an inducible mammalian expression vectors include pMSG, also available from Pharmacia (Piscataway, N.J., USA), and pTet-off and pTRE2 available from Clontech (Catalogue Nos K1620-A and 6241-1, respectively, Clontech, Palo Alto, Calif., USA). The pMSG vector uses the glucocorticoid-inducible promoter of the mouse mammary tumour virus long terminal repeat to drive expression of the cloned gene. The pTet-off and pTRE2 vectors use the presence or absence of tetracycline to induce protein expression via the tet-controlled transcriptional activator.

Host cells, for example murine Swiss 3T3 cells, that have been transformed by the recombinant DNA encoding the transglutaminase are then cultured for a sufficient time and under appropriate conditions to permit the expression of the transglutaminase and the subsequent cross-linking of ECM.

Thus, the kits of the invention may comprise a surface to which cross-linked ECM material may be adhered and cells capable of expressing a tissue transglutaminase, either endogenously or as a result of transfection (such as those identified above). Prior to using the kits, the cells are cultured in contact with the surface so as to deposit cross-linked ECM material on said surface.

Alternatively, cells which naturally express low levels of a tissue transglutaminase (or which do not naturally express a tissue transglutaminase) may be cultured and an exogenous tissue transglutaminase added in order to effect cross-linking of the ECM. Thus, in one embodiment, the kits of the invention may comprise a surface to which cross-linked ECM material may be adhered, cells which naturally express low levels of a tissue transglutaminase (or which do not naturally express a tissue transglutaminase), and an exogenous tissue transglutaminase. The exogenous tissue transglutaminase may be derived from natural sources (e.g. human tissue or cells such as lung, liver, spleen, kidney, heart muscle, skeletal muscle, eye lens, endothelial cells, erythrocytes, smooth muscle cells, bone and macrophages) or may be produced by recombinant means (as described above).

It will be appreciated by persons skilled in the art that, in the methods and kits of the invention, the surface to which the cross-linked ECM material is adhered (or is to be adhered) may take one of a number or forms. For example, the surface may be interior surface of a test tube or vial or the like. Alternatively, the surface may be concave surface of a well in a single- or multi-well plate, for example a microtitre plate.

Preferably, the surface is a multi-well plate such as a 96 well, flat bottomed, tissue culture treated plate (Product code M9780, Sigma Aldrich Company Ltd, Fancy Road, Poole, Dorset BH12 4QH, UK).

In a preferred embodiment of the second aspect of the invention, the kit further comprises a negative control sample. Preferably, the negative control sample is a serum sample or saliva sample from a healthy individual. Conveniently, the control sample is lyophilised serum or saliva.

Suitably, the control sample is an artificial or synthetic sample, such as bovine serum albumin.

Conveniently, the kit further comprises a positive control sample containing antibodies which are capable of binding to cross-linked ECM and, hence, will provide a positive test result against which the sample to be tested may be compared.

In an additional preferred embodiment of the second aspect of the invention, the kit further comprises a secondary antibody. By 'secondary antibody' we mean an antibody which can used to detect antibodies from the sera samples (i.e. primary antibodies) which have bound to the cross-linked ECM.

Preferably, the secondary antibody is an anti-human IgA antibody.

Alternatively, the secondary antibody is an anti-human IgG antibody.

In a preferred embodiment of the second aspect of the invention, the kit of parts is suitable for use in an ELISA.

Hence, the kit preferably comprises a secondary antibody which comprises a detectable moiety such as a fluorescent label, radiolabel or enzyme. The detectable moiety may be linked to the secondary antibody directly or via a linker moieties such as biotin-avidin.

Preferably, the secondary antibody is a goat anti-human IgA (α) antibody conjugated to horse radish peroxidase (e.g. Cat. Number 31417ZZ, Pierce Chemical Co, Rockford, Ill., USA).

Advantageously, the kit further comprises a horse radish peroxidase substrate, for example o-phenylebediamine dihydrochloride in acid-buffered $H_2O_2$.

Preferably, the kit further comprises a stop reagent such as sulphuric acid to quench the reaction of the horse radish peroxidase with the horse radish peroxidase substrate.

Conveniently, the kit further comprises a blocking agent such as defatted milk powder to block non-specific sites in the cross-linked ECM material.

Advantageously, the kit further comprises a washing agent such as a detergent to remove cellular material from the surface to which the ECM is adhered. For example, the washing agent may comprise a Tween® (e.g. Tween® 20), Triton-X100, CHAPS, CTAB or ammonium hydroxide solution. Preferably, the washing agent/detergent is dissolved in phosphate-buffered saline.

Preferred embodiments of the invention will now be described with reference to the following figures.

Key: CUB—anti-transglutaminase Type 2 murine monoclonal antibody, CUB 7402 (Neomarkers), diluted 1/1000.
FN—polyclonal rabbit anti-fibronectin (Sigma F3648) at 1/1000.

Key: TX100—0.1% Triton X-100. CTAB—0.01% CTAB, CHAPS—0.01% CHAPS, ammonium hydroxide—20 mM ammonium hydroxide in 0.1% Triton X-100.

EXAMPLES

Materials and Methods

Preparation of Transfected Swiss 3T3 Cells

In one embodiment, the ECM plate assay for the diagnosis of coeliac disease is based on the use of murine Swiss 3T3 fibroblast cells transfected with the gene for human type II transglutaminase (hTG) to produce a cross linked extracellular matrix rich in hTG. The cells are cultured directly into the multiwell plates to be used in the assay so that the ECM can be prepared as an antigen in an antibody capture type ELISA by the simple removal of the cells. This is made possible by the removal of other cellular materials with a detergent extraction with 0.1% sodium deoxycholate in phosphate buffered saline (or an equivalent buffer) for 10 minutes at room temperature. Other detergents (Triton X-100, CHAPS, CTAB) and ammonium hydroxide (known to be efficient as preparing ECM from cultured cells) have also been used with equal success. The critical requirement here is that the modified ECM is left intact on the bottom of the well while the remaining cellular materials are removed.

Cell Lines

3T3 Swiss Albino mouse embryo fibroblasts were obtained from the European Collection of Animal Cell Cultures (ECACC). They were cultured in Dulbecco's modified Eagle's medium (DMED4, Sigma-Aldrich Co Ltd, Poole, Dorset, UK) containing 10% fetal calf serum (FCS), 2 mM glutamine, 100 U/ml of penicillin and 100 μg/ml of streptomycin. Cells expressing the tetracycline-controlled transactivator (tTA) were kept in medium supplemented with 400 μg/ml active G418 (Geneticin; GIBCO BRL, Life Technologies Ltd, Paisley, Scotland, UK). Stable cell lines originating from tTA and expressing tissue transglutaminase were cultured in medium further supplemented with 250 μg/ml xanthine (Sigma-Aldrich Co Ltd), 15 μg/ml hypoxanthine, 10 μg/ml thymidine, 2 μg/ml aminopterin, and 10 μg/ml mycophenolic acid (GIBCO-BRL, Life Technologies Ltd).

Plasmid Vectors

The expression plasmid pUHD15-1 encoding tTA under the control of the HCMV promoter/enhancer, pUHC13-3 encoding luciferase under the control of the tTA-dependent minimal promoter hCMV*-1 and the tTA-dependent expression vector pUHD10-3 containing PhCMV*-1, followed by a multiple cloning site, were generously provided by H Bujard (Zentrum fur Molekulare Biologie, Heidelberg, Germany).

The plasmid pUHD10-3-TG was constructed by inserting the full length human tissue transglutaminase cDNA (Gentile et al, supra) into the EcoRI site of pUHD10-3.

The neomycin resistance plasmid pSVneo and the expression vector pSNFβGal encoding β-galactosidase were a gift of P. J. A. Davies (University of Texas Health Centre at Houston). The plasmid pUS1000 encoding XGPT (xanthine-guanine phosphoribosyltransferase) was donated by P Sanders (University of Surrey).

Transfections

Swiss 3T3 cell lines stably expressing the tetracycline-controlled transactivator (tTA clones) were generated using liposome-mediated transfection as previously described in Johnson et al, 1994, *Oncogene* 9:2935-2942. Cells ($1.0 \times 10^6$) were seeded into a 10-cm tissue culture petri dish 1 day prior to DNA transfer and then cotransfected with 9 μg of pUHD15-1 and 1 μg of pSVneo, using 100 μg of lipofectin per 10 μg of DNA (GIBCO-BRL, Life Technologies Ltd). Clones resistant to 800 μg/ml of active G418 (Geneticin, GIBCO-BRL, Life Technologies Ltd) were screened for tTA activity by transient transfection of pUHC13-3 using calcium phosphate (Kingston, 1990, In: *Current Protocols in Molecular Biology*, Ausubel et al. (Eds.), Greene-Wiley Interscience, New York) and then screened for luciferase activity (luciferase assay system, Promega Ltd, Southampton, UK). Light intensity was evaluated utilizing a scintillation counter and expressed in cpm per micrograms of protein. Transfection efficiency was normalized by cotransfection with 0.5 μg of PSVβgal and measurement of β-galactosidase activity (β-galactosidase assay system, Promega Ltd).

Positive clones were selected for further cotransfection with pUHD10-3-TG (9 μg) and the XGPT expression plasmid pUS1000 (μg) using lipofectin. Tetracycline (1 μg/ml) was included in the culture medium. Transfected clones resistant to selection medium for the salvage enzyme XGPT (250 μg/ml xanthine, 15 μm/ml hypoxanthine, 10 μg/ml thymidine, 2 μ/ml aminopterin, 10 μg.ml mycophenolic acid) were analysed for their capability to overexpress tissue transglutaminase (tTGase) by immunocytochemical staining, following withdrawal of tetracycline for 72 h. Clones were also screened for expression of tTGase by immunoprobing of Western blots of lysates as described previously (Johnson et al, supra). Western blots were probed using the monoclonal antibody to guinea pig liver enzyme Cub 7402 diluted 1/3000 in 0.1 M Tris-HCl, pH 7.4 (Birckbichler et al, 1985, *Hybridoma* 4:179-186) and revealed by chemiluminescence (Amersham International plc, Little Chalfont, Bucks, UK) using an anti-mouse IgG HRP conjugate. Guinea pig liver transglutaminase (Sigma-Aldrich Co. Ltd) was used as a tTGase standard. Protein concentration was determined using the method of Lowry.

Induction of Transglutaminase Expression in Transfected Cells

Cell lines stably transfected with transglutaminase containing pUHD10-3-TG were continuously cultured in the presence of tetracycline 2 μg/ml. To induce transglutaminase expression, exponentially growing cells were cultured in the absence of tetracycline for a minimum of 72 h and a maximum of 96 h. Parallel control cultures grown identically, keeping tetracycline in the medium. During the period of induction, culture medium was changed every 48 h.

Analysis of Transglutaminase Activity

Transglutaminase activity was measured as described in Lorand et al, 1972, *Anal. Biochem.* 50:623-631.

Cell Culture and Antigen Preparation

Culture of the transfected Swiss 3T3 cell line has been optimised to maximise the deposition of ECM in a form favourable to the endpoint of the assay. We have shown that the antigenic nature of the ECM prepared from these cells is optimal if one allows for complete induction of hTG in the first instance and for maturation of the ECM into a more 'tissue like' structure in the second instance. Immunofluorescent staining of cultured transfected Swiss 3T3 cells with coeliac sera has shown that the ECM antigen is most dense where the cells are confluent suggesting that antigen production is maximised during cell contact. We have found that cells cultured for 1 day past confluence produce ECM that is most suited for the assay.

Growing stocks of the transfected Swiss 3T3 cells are maintained in media designed to suppress expression of the hTG and to maintain the clonal identity of the cell line. The formula for this media is given below.

For every 500 ml of DMEM (Sigma 5546) remove 100 ml of media and add:

b) 50 ml foetal calf serum;
c) 10 ml 200 mM L-glutamine solution;
d) 10 ml 50× penicillin/streptomycin solution (10,000 units penicillin/10 mg streptomycin/ml);
e) 10 ml 50×HAT supplement (Sigma H8016);
f) 10 ml xanthine stock. Stock prepared by dissolving 250 mg of xanthine in 4 ml of 1M NaOH and adding 16 ml $dH_2O$;
g) 10 ml mycophenolic acid stock (prepared by dissolving 10 mg mycophenolic acid in 2 ml 1M NaOH and adding 18 ml $dH_2O$);
h) 2 ml G418 stock (prepared from powder at 1 g/10 ml in distilled water) and
i) 0.1% v/v tetracycline in distilled water.

As the tetracycline degrades in solution within 2 or 3 days, it is important to make up only enough complete media for each batch of culture. To maintain suppression of the hTG in culture the media should be replaced every other day. Induction of the hTG gene is simply achieved by replacing the culture media with similar fresh media free of the suppressor tetracycline. For the purposes of this example, the induced cells were left for 4 days (refreshing the media after 2 days) to ensure complete hTG induction. After the induction period, cells were transferred to the culture plates that were used in the assay, usually 96 well at a seeding density of 9000 cells per well and left incubated for a further 3 days. As these cells are adherent, it was necessary to use a standard trypsinisation step to remove the cells from the flask wall to enable sub-culturing and propagation.

To prepare the antigenic ECM, the culture medium must first be removed and the wells washed gently in phosphate buffered saline pH 7.4 (PBS). Unwanted cellular material is then removed by incubating each well with 100 µl of 0.1% sodium deoxycholate in PBS for 10 minutes. The well contents are then discarded and washed twice with PBS 0.2% Tween®-20 (PBST) followed by one wash with PBS. Non-specific binding sites are then blocked with 100 µl/well of 3% defatted milk powder (Marvel) in PBS (PBSM) for 30 minutes at 37° C. Plates can be stored at −20° C. in this state for at least one month. Longer storage may be possible.

The actual assay follows a basic protocol for an antibody capture assay as detailed below. It is envisaged that each kit may include negative and positive control sera (or saliva) consisting of screened human sera (or saliva). The negative control sample could be pooled from a group of positively identified non-coeliacs and the positive control sample would most likely consist of one high and one low titre coeliac serum or saliva. Both may be pre-diluted to the working concentration if possible. All samples and standards are to be assayed in triplicate.

1. Discard the blocking solution and add 50 µl per well of human serum to be tested diluted 1/500 in PBSM. Incubate for 2 hours at 37° C.
2. Wash twice with PBST and once with PBS.
3. Add 50 µl per well of anti-human IgA conjugated to HRP diluted appropriately in PBSM. For example, Pierce goat anti-human IgA (α chain specific) at 1/5000 in PBSM. Incubate for 2 hours at 37° C.
4. Wash twice with PBST and once with PBS.
5. Make up fresh HRP substrate based on o-phenylenediamine dihydrochloride (OPD) in acidified buffered $H_2O_2$. For example, one tablet of OPD (Sigma P3804, 5 mg/tablet) and 2 tablets of phosphate-citrate buffered urea $H_2O_2$ (Sigma P4560) to 20 ml d$H_2O$.
6. Plate out substrate solution at 50 µl per well and leave for 30 minutes at room temperature. Stop reaction with 50 µl per well of 2.5M $H_2SO_4$ and read plate at 492 nm.

Saliva samples may be assayed in a similar manner.

Example 1

1. Sera Used

FIRST BATCH: Obtained from Iain Murray, then of the City Hospital, Nottingham.

| Patient | Brief Pathology/Diagnosis |
| --- | --- |
| 12 | Untreated CD |
| 13 | Diarrhoea |
| 14 | Untreated CD (EMA+) |
| 15 | Diarrhoea, not CD |
| 18 | Normal |
| 27 | Normal |
| 53 | Untreated CD |

SECOND BATCH: Obtained from Iain Murray, then of Barnsley General Hospital.

| Patient | Brief Pathology/Diagnosis |
| --- | --- |
| 2 | CD with total villus atrophy |
| 3 | Normal |
| 4 | CD showing mild villus blunting, increased intra-epithelial lymphocytes and increased anti-gliadin antibodies |
| 9 | CD on a gluten free diet showing focal mild villus atrophy |
| 12a | Abnormal gut morphology but not indicative of CD |
| 13a | CD showing increased intra-epithehal lymphocytes and partial villus atrophy |
| 14a | CD showing total villus atrophy |
| 17 | CD showing total villus atrophy |

Supplemented by two samples from Nottingham Trent University post-graduate students, designated C1 and C2.

2. Method

As described above.

3. Results

Figure 1:
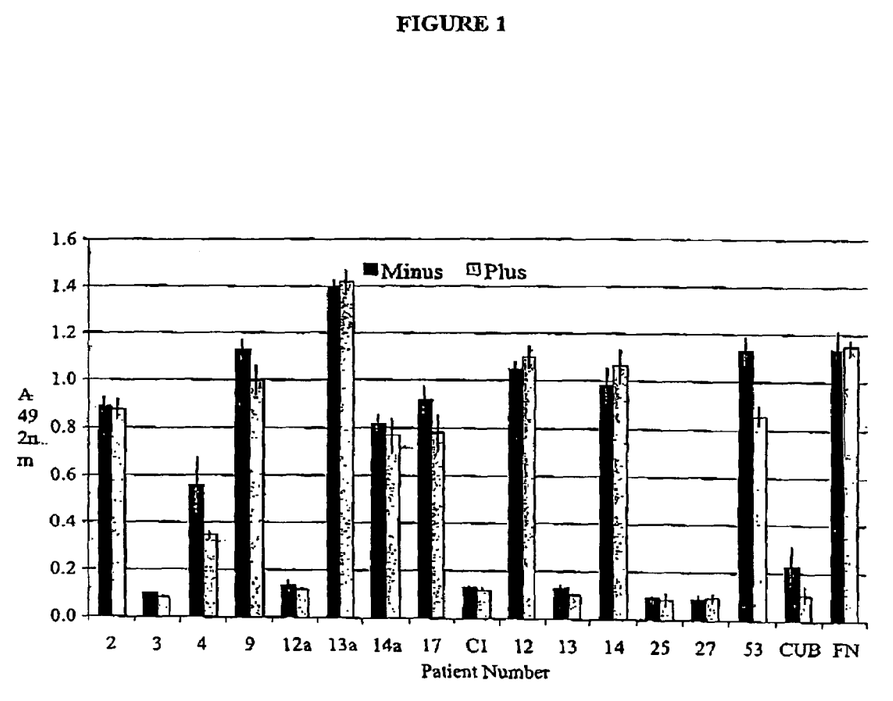
FIG. 1: ECM ELISA of human serum diluted 1/500 in which TGase induced cells (minus tetracycline in medium) are compared with TG non-induced cells (plus tetracycline in medium).

FIG. 1 shows data from an ECM ELISA of human serum diluted 1/500. TG induced cells (minus tetracycline in medium) are compared with TG non-induced cells (plus tetracycline in medium).

The results shown in FIG. 1 are typical of those obtained with ECM derived from Swiss 3T3 fibroblasts. All sera from patients diagnosed by biopsy as suffering from coeliac disease give large absorbance values when compared with the controls and known non-coeliac sera. Note that an indirect ELISA of these sera against human serum albumin, i.e. an unrelated antigen, gave signals similar to those found with the controls. Thus, the signals obtained with the controls and non-coeliac sera can be considered to represent the level of background for this assay. For example, it is possible to determine positive signals simply as those that are at least twice the average background.

An observable difference between induced type II TG and non-induced type II TG was limited to patients 4 and 53 and was only 10-20% of the signal, suggesting that antigenic TG is not the most significant antigen in this assay. Table 1 shows the results of other indirect ELISAs with guinea pig liver TG or human fibronectin as antigens compared with ECM and a control of human serum albumin for some of the sera. Anti-fibronectin activity of the sera was looked at as this protein is recognised as a principal constituent of the ECM and we hypothesised that anti-fibronectin antibodies were likely components in a complex polyclonal anti-ECM antibody profile. Even with this small sample of sera this simple comparison has illustrated deficiencies in the single antigen approach. Patients 14 and 17 were negative in the gpTG assay but were positive in the ECM assay and patients 4 and 9 were negative in the fibronectin assay but were positive in the ECM assay. It is particularly interesting to note that patient 4 is assayed as negative with gpTG and fibronectin but is positive (in accordance with the clinical diagnosis) in the ECM based assay. It was also noted that the fibronectin based assay was prone to weak false positives with two patients, numbers 3 and 12 giving incorrect results.

TABLE 1

EMC ELISA compared to simple indirect ELISAs human serum albumin (HSA), guinea pig liver transglutaminase (gpTG), and human fibronectin. TVA—total villus atrophy, PVA—partial villus atrophy.

| Patient | HSA | gpTG | FN  | ECM- | Pathology |
|---------|-----|------|-----|------|-----------|
| 2       | −   | +++  | ++  | +++  | TVA       |
| 3       | (+) | −    | +   | −    | Normal    |
| 4       | −   | −    | −   | +    | PVA       |
| 9       | −   | ++   | −   | ++   | PVA       |
| 12      | −   | −    | +   | −    | Abnormal  |
| 13      | −   | ++   | ++  | +++  | PVA       |
| 14      | −   | −    | +   | ++   | TVA       |
| 17      | ++  | (+)  | +++ | +++  | TVA       |
| 25      | −   | −    | −   | −    | Normal    |
| C1      | −   | −    | −   | −    | Control 1 |
| C2      | −   | −    | −   | −    | Control 2 |

Key:
− Background,
(+) Weak positive,
+ Low Positive,
++ Medium Positive,
+++ High Positive.

Based on these data we are proposing that the improvement in the cell matrix assay over existing assays comes from the antigen being more like the material that may be targeted by the immune system during the progression of coeliac disease. That is to say that although type II TG has been shown to be an antigen in most cases of coeliac disease our results support the findings of other researchers that have shown that TG is not the only antigen and that this may be exploited to produce a broader based assay.

Example 2

1. Sera Used

See Example 1.

2. Method

This method is essentially the same as that given previously except that 0.1% Triton X-100, 0.01% CTAB, 0.1% CHAPS and 20 mM ammonium hydroxide with 0.1% Triton X-100 replace the 0.1% sodium deoxycholate.

3. Results

Figure 2:
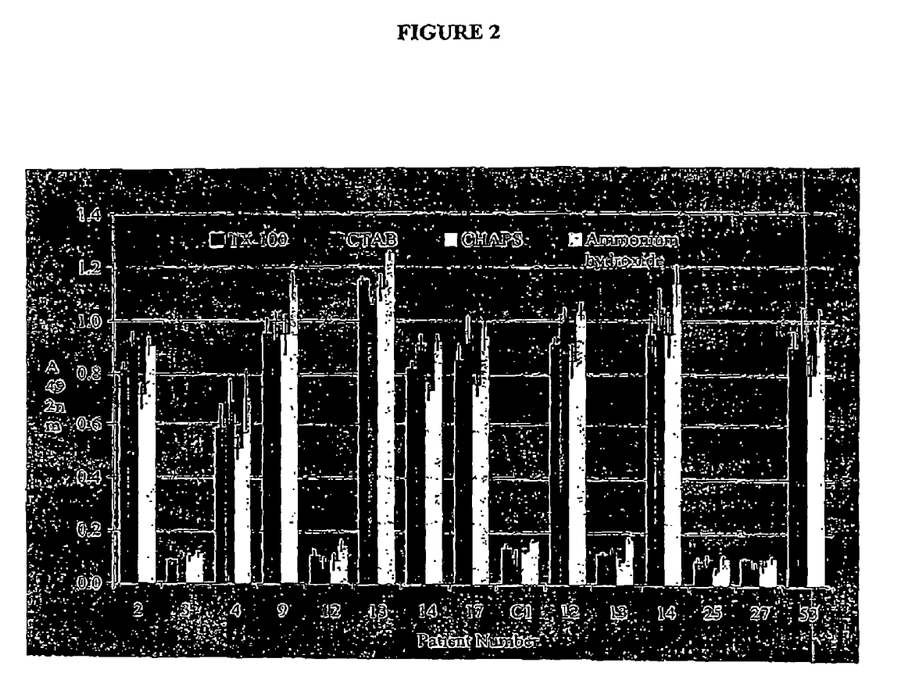
FIG. 2: ECM ELISA of human serum diluted 1/500 showing the effect on the assay of using a variety of extractants to prepare the ECM.

FIG. 2 shows data from an ECM ELISA of human serum diluted 1/500 to show the effect on the assay of using a variety of extractants to prepare the ECM.

The data in FIG. 2 show that the endpoint of the assay is essentially independent of the method used to prepare the matrix proteins for use in the assay. For the assay to work, the extraction needs to remove the general bulk of the cellular material and leave matrix proteins behind in a way that preserves the antigenic qualities of this material. The variation that is evident in FIG. 2 can be attributed to natural fluctuations in the character of the cell matrix as it is laid down and to general inter-assay variations that occur in all ELISAs before proper normalisation has been applied. Even so, this amount of variation in the endpoint does not prove to be a problem when identifying positive sera.

Example 3

1. Sera Used

Second batch of sera used in Example 1.

2. Method

Screened primary cultures of human foreskin dermal fibroblasts (preferably not older than passage 10) were maintained in complete DMEM (Sigma 5546) containing 10% FCS, 2% 200 mM L-glutamine solution and 2% penicillin/streptomycin solution (10,000 units penicillin, 10 mg streptomycin/ml) using standard tissue culture methods. Cells were transferred to the culture plates that were used in the assay, usually 96 well, at a seeding density of 10000 cells per well and left to incubated for a further 3 days. As these cells are adherent, it is necessary to use a standard trypsinisation step to remove the cells from the flask wall to enable subculturing and propagation.

3. Results

Figure 3:
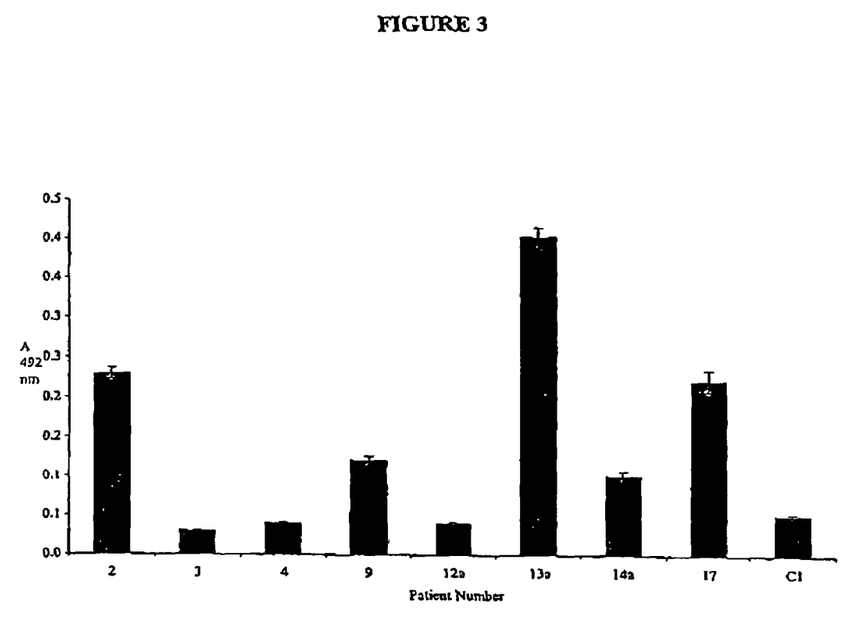
FIG. 3: ELISA of ECM prepared from human dermal fibroblasts with human serum diluted 1/500.

FIG. 3 shows data from the ELISA of ECM prepared from human dermal fibroblasts with human serum diluted 1/500.

On the whole, the results with the human foreskin dermal fibroblast generated ECM mirrored those seen with the 3T3 derived ECM. However, as can be seen in FIG. 3, the signal is diminished to the point where patient 4 is not distinguishable from the control.

The invention claimed is:

1. A method for diagnosing coeliac disease in a patient comprising:
   (a) contacting an antibody sample from said patient with insoluble cross-linked extracellular matrix (ECM) material immobilised on a surface, wherein the ECM material is derived from cells which express a tissue transglutaminase and comprises proteins selected from the group consisting of fibronectin, vitronectin, collagens, latent TGFβ-1 binding protein (LTBP-1), fibrillins, elastin and laminin,
   wherein said ECM is treated prior to use to remove non-ECM cellular material; and
   (b) detecting binding of two or more types of antibodies present in the sample to the immobilised ECM material, each type of antibody having affinity for a different protein component of the cross-linked ECM, wherein the binding of antibodies present in the sample to the immobilised ECM material is indicative of a positive diagnosis.

2. A method according to claim 1 wherein the antibody sample is a serum sample.

3. A method according to claim 1 wherein step (b) comprises detecting binding of IgA antibodies to the immobilised ECM material.

4. A method according to claim 1 further comprising repeating steps (a) and (b) with a negative control sample.

5. A method according to claim 4, wherein the negative control sample is a serum sample or saliva sample from a healthy individual.

6. A method according to claim 4 wherein a positive diagnosis is made when the level of binding of antibodies present in the patient's antibody sample to the immobilised ECM material is at least 20% greater than the level of binding of antibodies present in the negative control sample.

7. A method according to claim 6 wherein a positive diagnosis is made when the level of binding of antibodies present in the patient's antibody sample to the immobilised ECM material is at least 100% greater than the level of binding of antibodies present in the negative control sample.

8. A method according to claim 6, wherein a positive diagnosis is made when the level of binding of antibodies present in the patient's antibody sample to the immobilised ECM material is at least 200% greater than the level of binding of antibodies present in the negative control sample.

9. A method according to claim 1 wherein step (b) comprises using an ELISA.

10. A method according to claim 9 wherein the ELISA comprises using an anti-human IgA antibody.

11. A method according to claim 1 wherein the cells are transfected with a nucleic acid molecule encoding a tissue (type II) transglutaminase.

12. A method according to claim 11 wherein the cells are Swiss 3T3 cells.

13. A method according to claim 1 wherein the tissue transglutaminase is human type II transglutaminase.

14. A method according to claim 1 wherein the surface is a multi-well plate.

15. A method according to claim 1, wherein the ECM material is derived from cells transfected with a nucleic acid molecule encoding a transglutaminase.

* * * * *